(12) United States Patent
List et al.

(10) Patent No.: US 12,721,548 B2
(45) Date of Patent: Sep. 1, 2026

(54) MODULAR IMPLANTABLE MEDICAL DEVICE

(71) Applicant: Roche Diabetes Care, Inc., Indianapolis, IN (US)

(72) Inventors: Hans List, Oberzent (DE); Frederic Wehowski, Hockenheim (DE)

(73) Assignee: Roche Diabetes Care, Inc., Indianapolis, IN (US)

( * ) Notice: Subject to any disclaimer, the term of this patent is extended or adjusted under 35 U.S.C. 154(b) by 753 days.

(21) Appl. No.: 17/187,330

(22) Filed: Feb. 26, 2021

(65) Prior Publication Data

US 2021/0177314 A1 Jun. 17, 2021

Related U.S. Application Data

(63) Continuation of application No. PCT/EP2019/073078, filed on Aug. 29, 2019.

(30) Foreign Application Priority Data

Aug. 31, 2018 (EP) .................................... 18191878

(51) Int. Cl.
*A61B 5/145* (2006.01)
*A61B 5/00* (2006.01)
(Continued)

(52) U.S. Cl.
CPC .......... *A61B 5/14503* (2013.01); *A61B 5/076* (2013.01); *A61B 5/14532* (2013.01);
(Continued)

(58) Field of Classification Search
CPC .............. A61B 5/14532; A61B 5/1455; A61B 5/14865; A61B 5/0031; A61B 5/076;
(Continued)

(56) References Cited

U.S. PATENT DOCUMENTS 5,372,133 A 12/1994 Hogen Esch
5,733,313 A 3/1998 Barreras, Sr. et al.
(Continued)

FOREIGN PATENT DOCUMENTS

AU 2007258756 A1 12/2007
CN 1874048 A 12/2006
(Continued)

OTHER PUBLICATIONS

GOST R ISO 14708-1-2012 Group P26. Surgical implants. Active Implantable Medical Devices, 39 pages.
(Continued)

*Primary Examiner* — Aurelie H Tu
*Assistant Examiner* — Andrew E Hoffpauir
(74) *Attorney, Agent, or Firm* — Bose McKinney & Evans LLP

(57) ABSTRACT

An implantable medical device has an implantable power supply and an implantable medical unit. The implantable supply powers the device and it includes a hermetically sealed supply housing, a battery, and a supply power coupler that powers the implantable medical unit from the battery via a wireless coupling. The implantable medical device also has a hermetically sealed medical unit housing, and it includes a functional medical module including a continuous glucose meter module. In use, the implantable medical unit is releasably mechanically coupled to the implantable supply and a wireless coupling of a medical unit power coupler with a supply power coupler is made, thereby powering the medical unit from the battery of the implantable supply.

20 Claims, 4 Drawing Sheets

(51) Int. Cl.
*A61B 5/07* (2006.01)
*A61N 1/372* (2006.01)

(52) U.S. Cl.
CPC .... *A61B 5/6861* (2013.01); *A61B 2560/0219* (2013.01); *A61B 2560/0443* (2013.01); *A61N 1/37288* (2013.01)

(58) Field of Classification Search
CPC ........... A61B 5/24; A61B 5/287; A61B 5/686; A61B 2560/0214; A61B 2560/04; A61B 2560/0443; A61B 2560/0219; A61B 2562/162; A61N 1/375; A61N 1/378; A61N 1/37288; A61N 1/3758; A61M 2230/201; A61M 5/1723; A61M 5/14276
See application file for complete search history.

(56) References Cited

U.S. PATENT DOCUMENTS 6,088,608 A 7/2000 Schulman et al.
6,631,296 B1 10/2003 Parramon et al.
8,974,398 B2 * 3/2015 Smith .................... H01R 24/66 600/561
9,216,285 B1 * 12/2015 Boling ............... A61B 5/02444
9,393,432 B2 * 7/2016 Wahlstrand .......... A61N 1/3754
10,022,054 B2 * 7/2018 Najafi ................ A61B 5/02158
2004/0106963 A1 * 6/2004 Tsukamoto ......... H01M 10/613 607/33
2005/0187594 A1 8/2005 Hatlestad
2005/0261562 A1 * 11/2005 Zhou .................. A61B 5/14865 600/347
2006/0015024 A1 1/2006 Brister et al.
2007/0179552 A1 * 8/2007 Dennis .................. A61N 1/056 607/37
2008/0039904 A1 2/2008 Bulkes et al.
2008/0109044 A1 * 5/2008 Gramse ............. A61N 1/37512 607/36
2008/0281298 A1 11/2008 Andersen et al.
2009/0198307 A1 8/2009 Mi et al.
2009/0264965 A1 10/2009 Fowler et al.
2010/0076254 A1 3/2010 Jimenez et al.
2010/0099281 A1 * 4/2010 Weiss ..................... A61N 1/056 439/86
2012/0095528 A1 4/2012 Miller, III et al.
2012/0116190 A1 5/2012 Iketani et al.
2012/0235503 A1 9/2012 Kesler et al.
2013/0116763 A1 5/2013 Parker et al.
2013/0198531 A1 8/2013 Hansen et al.
2014/0187877 A1 7/2014 Emken et al.
2014/0378791 A1 12/2014 DeHennis et al.
2015/0073247 A1 3/2015 Gordon et al.
2016/0175590 A1 * 6/2016 Kulkarni .............. H04B 5/0075 607/57
2016/0325105 A1 * 11/2016 Etzkorn ............... A61N 1/3787
2017/0173345 A1 * 6/2017 Abiri ....................... H02J 50/50
2017/0203109 A1 7/2017 Maile et al.
2018/0028825 A1 2/2018 Leigh
2018/0036537 A1 2/2018 Van den Heuvel
2018/0050189 A1 * 2/2018 Rump ................ A61N 1/37229
2018/0184905 A1 7/2018 Riebel et al.
2019/0126051 A1 5/2019 Strommer et al.
2019/0269339 A1 * 9/2019 Najafi .................. A61B 5/0004
2020/0086117 A1 * 3/2020 Verzal .................... A61N 1/375

FOREIGN PATENT DOCUMENTS

CN 101352596 A 1/2009
CN 101980412 A 2/2011
CN 103328041 A 9/2013
CN 105530991 A 4/2016
EP 2 234 666 A2 10/2010
EP 3 010 415 A1 4/2016
JP H06-7324 A 1/1994
JP 2007-537841 A 12/2007
JP 2008-506469 A 3/2008
JP 2016-508761 A 3/2016
RU 151735 U1 4/2015
WO WO 2004/014214 A2 2/2004
WO WO-2007059343 A2 * 5/2007 ......... A61N 1/37518
WO WO 2009/048462 A1 4/2009
WO WO 2009/055856 A1 5/2009
WO WO 2011/001916 A1 1/2011
WO WO 2011/095229 A1 8/2011
WO WO 2014/035592 A1 3/2014
WO WO 2015/023291 A1 2/2015
WO WO 2016/178817 A1 11/2016
WO WO 2017/025606 A1 2/2017

OTHER PUBLICATIONS

International Search Report and Written Opinion of the International Searching Authority, PCT/EP2019/073078, Nov. 28, 2019, 10 pages.
Extended European Search Report, EP 18 191 878.0, Feb. 4, 2019, 9 pages.
Hui et al., Wireless Charging System of High Efficiency Implantable Stimulation Medical Devices, Power Supply Technology and Its Application, 2012, pp. 54-56.

* cited by examiner

MODULAR IMPLANTABLE MEDICAL DEVICE

RELATED APPLICATIONS

This application is a continuation of PCT/EP2019/073078, filed Aug. 29, 2019, which claims priority to EP 18 191 878.0, filed Aug. 31, 2018, the entire disclosures of both of which are hereby incorporated herein by reference.

BACKGROUND

This disclosure teaches an implantable medical device with an implantable medical unit and an implantable supply unit. This disclosure further relates to an implantable supply unit for electric power supply of an implantable medical unit as well as to a method for powering an implantable medical unit. One field of application is in implantable continuous glucose meters.

Implantable medical devices are widely known, for example, as heart pace makers, brain pacemakers, implantable infusion pumps, cochlea implants, or implantable measurement devices for body parameters such as glucose.

In the field of diabetes therapy, continuous glucose meters are being used in increasing numbers since they offer a number of advantages over so-called spot measurement devices based on test strips. Continuous glucose meters typically rely on an electrochemical measurement principle with a set of, e.g., three measurement electrodes that are placed in the tissue, and associated circuitry. In contrast to spot measurement devices, they provide glucose information continuously or quasi-continuously, e.g., every few minutes, and/or on demand.

Some available glucose meters are generally placed on the skin outside the body and comprise a subcutaneous or transcutaneous element that carries the electrodes. For such design, the power supply in the form of a battery is arranged together with circuitry in the portion outside the body, typically as a skin-adhesive patch. Since a continuous glucose meter is generally carried by a Person with Diabetes (PwD, also referred to as user) substantially continuously night and day, the skin of the user is permanently pierced by the transcutaneous element. This is known to cause side effects such as itching, eczema and in some cases even severe inflammation.

In order to avoid such drawbacks, fully implantable continuous glucose meters have been developed.

For such implantable continuous glucose meters as well as for other types of implantable medical devices, e.g., brain pacemakers or cochlea implants, powering the device by way of electric energy supply is a critical issue. For implantable devices with a built-in battery, the battery capacity is often the limiting factor for the lifetime of the overall device and accordingly determines the time after which the device needs to be explanted and replaced, even if other components are still intact and functional. If, on the other hand, the battery has a longer lifetime as compared to other components, the battery capacity cannot be fully exploited. This is particularly critical in devices where the costs of the battery are comparatively high in comparison to the total device costs, as it is the case, e.g., for typical implantable continuous glucose meters.

In order to improve the situation regarding the power supply, implantable medical devices have been developed that do not have an autonomous power supply in form of a battery, but are continuously powered transcutaneously by way of inductive coupling via an extracorporeal supply unit that is placed on the skin. Since, however, the location of the implanted device is determined by the implantation site and accordingly fixed, the supply unit also needs to be arranged on the skin at a corresponding fixed position, typically as adhesive patch. This continuous attachment of the supply unit also causes effects such as itching, eczema and in some cases inflammation.

EP 3 010 415 discloses a measurement system wherein a sensor and a transmitter are fully implantable and are connected via cable. The sensor and the transmitter are positioned in different regions of the body. This has the drawback that implantation and explanation of the system requires a surgery at at least two positions of the patient's body. Also, the cable can cause inconvenience for the patient and there is a risk of a cable failure.

EP 2 234 666 discloses a fully implantable medical device comprising a transmitter module with a cable and a battery module that is detachably connected with the transmitter module via the cable. This allows the battery module to be easily disconnected from the transmitter module and, therefore, to be easily exchanged. However, there is a risk of a failure of the cable.

U.S. Publication No. 2018/0028825 discloses an implantable hearing system wherein the main implant module which comprises a battery and a transceiver is implanted, as well. The main implant module is connected to the receiver coil and the stimulating assembly via cable. Thus, there is a risk of a failure of the cable. Also, the data and energy transfer is of comparatively low efficiency.

WO 2015/023291 A1 concerns the powering of cochlear implants. In an embodiment, a cochlear implant module and a separate battery module are provided. A junction connector provides a non-galvanic and releasable coupling via inductive power transfer. In a further embodiment, an implantable overmold comprises an implantable sound processor and a battery and is coupled with an implantable cochlea implant module via a connector junction and a cable.

U.S. Publication No. 2017/173345 A1 concerns the powering of a long term implantable medical device. The disclosed arrangement includes an implantable functional unit, an implantable secondary power unit and an extracorporeal primary power unit. From the primary power unit, power is provided to the secondary power unit and from the secondary power unit to the functional unit via inductive coupling.

WO 2016/178817 A1 discloses an implantable system with a battery package and an electronic device that may both be implanted into the body and be coupled via a magnetic alignment structure. The electronic device is powered from the battery package via wireless power transceivers with inductive coupling.

SUMMARY

This disclosure teaches improvements regarding the power supply of implantable devices. Favorably, the before-mentioned drawbacks of the state of the art can be reduced or avoided.

An implantable supply unit for use in combination with an implantable medical unit in accordance with the present disclosure may include:

a) a hermetically sealed supply unit housing;

b) a battery;

c) a supply unit power coupler, the supply unit power coupler being configured for powering the medical unit from the battery by way of non-galvanic coupling;

d) a supply unit data coupler, the supply unit data coupler being configured for non-galvanic data communication with the medical unit;
e) a supply unit communication interface, the supply unit communication interface being configured for non-galvanic data communication with a non-implanted remote device;
f) a supply unit coupling arrangement, the supply unit coupling arrangement being configured for releasable mechanical coupling the medical unit to the supply unit.

The battery, the supply unit power coupler, the supply unit data coupler and the supply unit communication interface are enclosed by the supply unit housing.

The expression "implantable" in the context of a device or unit refers to the device or unit being designed and adapted to be fully located within in a human or animal body in a way that it is fully enclosed by tissue and without any part of the device or unit being located outside the body and in particular without piercing the skin. The expressions "implantable" and "fully implantable" are accordingly to be understood as synonyms where not explicitly stated differently.

The term "non-galvanic" refers to a power and/or data transmission that does not rely on a galvanic respectively conductive coupling by wiring or electrical contacts. It is therefore to be understood as equivalent to "wireless."

The supply unit power coupler is operatively coupled with the battery, typically by way of galvanic coupling respectively wiring directly or via further circuitry. In a situation of use, the medical unit power coupler receives power from the supply unit power coupler by way of non-galvanic coupling and electrically powers the medical unit with the received power.

For purposes of this disclosure, the terms "supply unit," "supply," "implantable supply" and "implantable supply unit" are used interchangeably. The supply unit typically further includes a control circuit. The control circuit is designed to control the overall operation of the supply unit and a medical unit that is coupled to the supply unit in an operable state. The control circuit typically includes one or more programmable components, such as microcomputers and/or microprocessors running a corresponding firmware code, application specific integrated Circuits (ASICs), and/or further electronics components as generally known in the art.

In a situation of use, the supply unit data coupler operatively couples with a medical unit data coupler of a medical unit as counter element. The data communication may be unidirectional or bidirectional. In embodiments where the medical unit includes a diagnostic module for acquiring one or more body parameters such as a glucose value in case of the medical unit including a continuous glucose meter module, data reflecting the one or more body parameters may be transmitted from the medical unit to the supply unit. In embodiments where the medical unit includes a therapeutic module or stimulation module, such as a cochlea stimulation implant module, a brain pacemaker module, or a retinal implant module, data corresponding to the required stimulation may be transmitted from the supply unit to the medical unit. Data communication between the supply unit and the medical unit may be continuously or non-continuously respectively sporadic. By way of example, data corresponding to a glucose value may be transmitted within a predetermined time interval for the medical unit being or including a continuous glucose meter, and/or upon a corresponding request by the supply unit.

The supply unit communication interface serves for the purpose of wireless data communication with a non-implanted remote device in a situation of use. A remote device communication interface of the remote device serves as counter element for the supply unit communication interface. Data communication between the supply unit communication interface and the remote device communication interface may be based on any wireless technology that is suited for data communication through skin and tissue, such as Near Filed Communication (NFC), Bluetooth, Wi-Fi and/or a proprietary Radio Frequency (RF) coupling. A remote device may be a general-purpose device, such as a Smart Phone, that includes a suited remote device communication interface and hosts a corresponding application, or may be a dedicated special-purpose device.

In a situation of use, the remote device serves as user interface and controls operation of the implanted medical device and/or receives data from the medical device. By way of example, the remote device may receive data reflecting measured glucose levels in case of the medical unit including a continuous glucose meter module. Communication between the implantable medical device respectively its supply unit and the remote device may be unidirectional or bidirectional. Further, the communication may be continuous or non-continuous or sporadic, for example initiated by a user command.

In a situation of use, the supply unit coupling arrangement mechanically couples with corresponding mechanical unit coupling arrangement of a medical unit as counter element such that the supply unit and the medical unit form a common compact assembly that can be implanted into and removed from the body. In the coupled state, the supply unit and the medical unit are favorable rigidly connected, at least held in a relative position to each other with limited possibility of movement. The expression "releasable mechanical coupling" refers to a coupling that may be separated with or without the use of additional tools such that at least one of the medical supply unit and the medical unit stays intact (i.e., is not destroyed or damaged) and can accordingly be subsequently reused. In some embodiments, both of the supply unit and the medical units stay intact. The supply unit coupling arrangement and the corresponding medical unit coupling arrangement may, by way of example, be realized by or include a bayonet, a threaded coupling, a snap-fit, or a force fit. If desired, either of both of the supply unit coupling arrangement and/or the medical unit coupling arrangement may include elastically or plastically deformable elements, such as deformable ribs, fingers, bars, a sleeve, or the like.

A supply unit of the above-described type provides, in combination with a corresponding medical unit, a particular favorable architecture for an implantable medical device. In the context of an overall design where the therapeutic and/or diagnostic functional modules or units have a longer lifetime as compared to other units or elements, in particular the battery, one and the same medical unit may be used in combination with a number of supply units in sequence. If, to the contrary, the supply unit has a longer lifetime as compared to the medical unit, one and the same supply unit may be used in combination with a number of medical units in sequence. This latter scenario is typical for example where the medical unit includes sensing and/or stimulation electrodes that degrade over time and/or are encapsulated by tissue in a way that functionality is reduced or even lost. Further advantages of particular embodiments are discussed below in context.

In a particular embodiment of the implantable supply unit, the supply unit power coupler is formed integrally with the supply unit data coupler. In such embodiments, a common coupling device, e.g., in form of a coil, serves as both supply unit power coupler and supply unit data coupler for both wireless power transmission to the medical unit and wireless data communication with the medical unit. Typically, the operative coupling is realized as inductive coupling in such embodiments.

Alternatively, however, the supply unit power coupler and the supply unit data coupler are distinct. In such embodiments, the supply unit power coupler is designed for coupling with a medical unit power coupler as counter element for power transmission purposes. The supply unit data coupler is designed for separate coupling with a medical unit data coupler for data transmission purposes. In such embodiments, power and data transmission are accordingly realized separately. Power transmission and data transmission may, for example, be realized via inductive capacitive, or optic. The type of coupling may be identical or different for power transmission and data transmission.

In a particular embodiment of the implantable supply unit, the battery is a rechargeable battery and the implantable supply unit includes a charging coupler for non-galvanic charging the battery in an implanted state of the supply unit.

This type of embodiment is particularly favorable since it allows a use of medical device over an extended time period of, e.g., a number of years, without the need for a corresponding extracorporeal charging device being permanently attached adjacent to respectively in proximity to the body. A charging device for transcutaneous powering an implantable device in the implanted state is typically attached to the skin by way of adhesive. While a variety of generally skin-friendly adhesives is available, the long-term use of such adhesives at one and the same position is an issue of concern and may cause skin moderate or severe skin-irritations, itching, eczema, or the like as explained before. In this context it is noted that transcutaneous power supply of an implanted device requires the charging device to be placed on the skin in substantially the same position.

For the above-described type of embodiment, a charging device needs to be attached to the body only temporarily and occasionally and for a limited time period for charging the battery. By way of example, the battery may be dimensioned such that recharging is only occasionally required. Intervals between a week and a month are most practical, but even daily is possible. In a typical technical implementation, the charging coupler is realized by a charging coil that couples with a supply coil of a charging device for charging the battery by way of transcutaneous inductive coupling.

In a particular embodiment of the implantable supply unit, the charging coupler is formed integrally with the supply unit communication interface. In such embodiment, the supply unit communication interface serves additionally as charging coupler, typically by way of inductive coupling. In further embodiments, the supply unit communication interface and the charging coupler are distinct from each other.

In a particular embodiment of the implantable supply unit, the supply unit power coupler includes a supply unit power coupler coil. In such embodiments, a medical unit includes a medical unit power coupler coil as counter element and wireless power supply of the medical unit is realized by way of inductive coupling. In other embodiments, wireless power supply of the medical unit is realized by way of capacitive coupling. In such embodiments, the supply unit power coupler includes corresponding supply unit power coupler electrodes and the medical unit may include corresponding medical unit power coupler electrodes as counter element. In still further embodiments, wireless power supply of the medial unit is realized by way of optical coupling, using, e.g., IR radiation. In such embodiment, a Light Emitting Diode (LED) in the supply unit may serve as supply unit power coupler and a photo diode in the medical unit may serve as medical unit power coupler. In accordance with the present disclosure, the medical unit is in any case passive in that it does not comprise its own power supply but is designed to by powered from the supply unit.

In a particular embodiment of the implantable supply unit, the supply unit coupling arrangement includes a receiving recess in the supply unit housing for receiving at least part of the medical unit. This type of arrangement allows a particularly compact and robust overall design and provides options for a favorable arrangement of the supply unit data coupler and supply unit power coupler as well as their corresponding counter elements in the medical unit, such that efficient and reliable coupling is achieved.

In a particular embodiment with a supply unit power coupler coil and a receiving recess as explained before, the supply unit power coupler coil is arranged circumferentially around the receiving recess. This type of arrangement allows a design where, in a coupled state of the supply unit and a medical unit respectively in a situation of use, the supply unit power coupler coil and a medical unit power coupler coil are cylinder coils, with the supply unit power coupler coil being arranged around the medical unit power coupler coil in a coaxial manner with or without axial offset.

An implantable medical device in accordance with the present disclosure may include an implantable supply unit and an implantable medical unit. The supply unit of the implantable medical device may generally be designed according to any embodiment as discussed above and/or further below. The implantable supply unit includes:

a. a hermetically sealed supply unit housing;
b. a battery;
c. a supply unit power coupler, the supply unit power coupler being configured for powering the implantable medical unit from the battery by way of non-galvanic coupling;
d. a supply unit data coupler, the supply unit data coupler being configured for non-galvanic data communication with the medical unit;
e. a supply unit communication interface, the supply unit communication interface being configured for non-galvanic communication with a non-implanted remote device;
f. a supply unit coupling arrangement, the supply unit coupling arrangement being configured for releasable mechanical coupling the medical unit to the supply unit.

The battery, the supply unit power coupler, the supply unit data coupler and the supply unit communication interface are enclosed by the supply unit housing.

The medical unit of the implantable medical device includes:

a. a hermetically sealed medical unit housing;
b. a functional medical module;
c. a medical unit power coupler, the medical unit power coupler being configured to receive power from the supply unit power coupler by way of non-galvanic coupling, thereby powering the medical unit;
d. a medical unit data coupler, the medical unit data coupler being configured for non-galvanic data communication with the supply unit;

e. a medical unit coupling arrangement, the medical unit coupling arrangement being configured as counter element for the supply unit coupling arrangement.

Both the supply unit and the medical unit may be of any design as discussed above and/or further below in the general description as well as exemplary embodiments.

The hermetically sealed medical unit housing generally encloses the components of the medical unit, in particular the medical unit power coupler and the medical unit data coupler, as well as any further medical unit circuitry. The functional medical module typically includes circuitry that is also enclosed by the medical unit housing. The functional medical module, however, typically has some interface to the outside, e.g., in the form of sensing and/or stimulation electrodes.

In a particular embodiment of the implantable medical device, the supply unit power coupler includes a supply unit power coupler coil and the medical unit power coupler includes a corresponding medical unit power coupler coil. In a typical realization, the supply unit power coupler coil and medical unit power coupler coil are NFC coils.

In a particular embodiment with a supply unit power coupler coil and a corresponding medical unit coupler coil, the medical unit includes a ferromagnetic coupling member and the medical unit power coupler coil is arranged circumferentially around the ferromagnetic coupling member. The ferromagnetic coupling member is typically shaped as a rod or bar and is made of a material of high magnetic permeability, such as ferrite. In a coupled state of the supply unit and the medical unit respectively in a situation of use, the supply unit power coupler coil is favorable arranged circumferential around the medical unit power coupler coil. This results in a coaxial arrangement with the ferromagnetic coupling member in the center, the supply unit power coupler coil forming the periphery and the medical unit power coupler coil being arranged radially between the ferromagnetic coupling member and the supply unit power coupler coil.

Since the supply unit power coupler is enclosed by the supply unit housing and the medical unit power coupler is enclosed by the medical unit housing, corresponding wall elements of the supply unit housing and the medical unit housing are arranged, in a situation of use, between the supply unit power coupler and the medical unit power coupler. The wireless coupling and power transmission is accordingly effected through the wall elements of the supply unit housing and medical unit housing, respectively.

In a particular embodiment of the implantable medical device with a ferromagnetic coupling member, the medical unit housing includes an elongated medical unit housing member, wherein the ferromagnetic coupling member is enclosed by the elongated medical unit housing member, and wherein the supply unit housing includes a receiving recess, wherein the receiving recess is configured to receive at least part of the elongated medical unit housing member, and wherein the supply unit power coupler coil is arranged circumferentially around the receiving recess.

The arrangement of the elongated housing member and a corresponding receiving recess may also be reversed in alternative embodiments. That is, the supply unit housing may include an elongated supply unit housing member while the medical unit may include a corresponding receiving recess. Further in such embodiment, a ferromagnetic coupling member may be enclosed by the elongated supply unit housing member.

In accordance with this disclosure, the functional medical module is or includes a continuous glucose meter module. In an alternative embodiment of this disclosure, or additionally, the functional medical module is or includes a cochlea implant module, a brain pacemaker module or a retinal implant module. The present disclosure is, however not limited to these particular types of functional modules.

A method for powering an implantable medical unit in accordance with the present disclosure may include:

a) releasable mechanical coupling the implantable medical unit and an implantable supply unit;
b) non-galvanic coupling a medical unit power coupler of the medical unit with a supply unit power coupler of the supply unit, thereby powering the medical unit from a battery of the supply unit.

The implantable medical unit and the implantable supply unit may be designed according to combination of corresponding respectively matching embodiments as discussed above and/or further below.

In a particular embodiment of the method, the non-galvanic coupling is an inductive coupling.

BRIEF DESCRIPTION OF THE DRAWINGS

The above-mentioned aspects of exemplary embodiments will become more apparent and will be better understood by reference to the following description of the embodiments taken in conjunction with the accompanying drawings, wherein.

DESCRIPTION

The embodiments described below are not intended to be exhaustive or to limit the invention to the precise forms disclosed in the following detailed description. Rather, the embodiments are chosen and described so that others skilled in the art may appreciate and understand the principles and practices of this disclosure.

Figure 1:
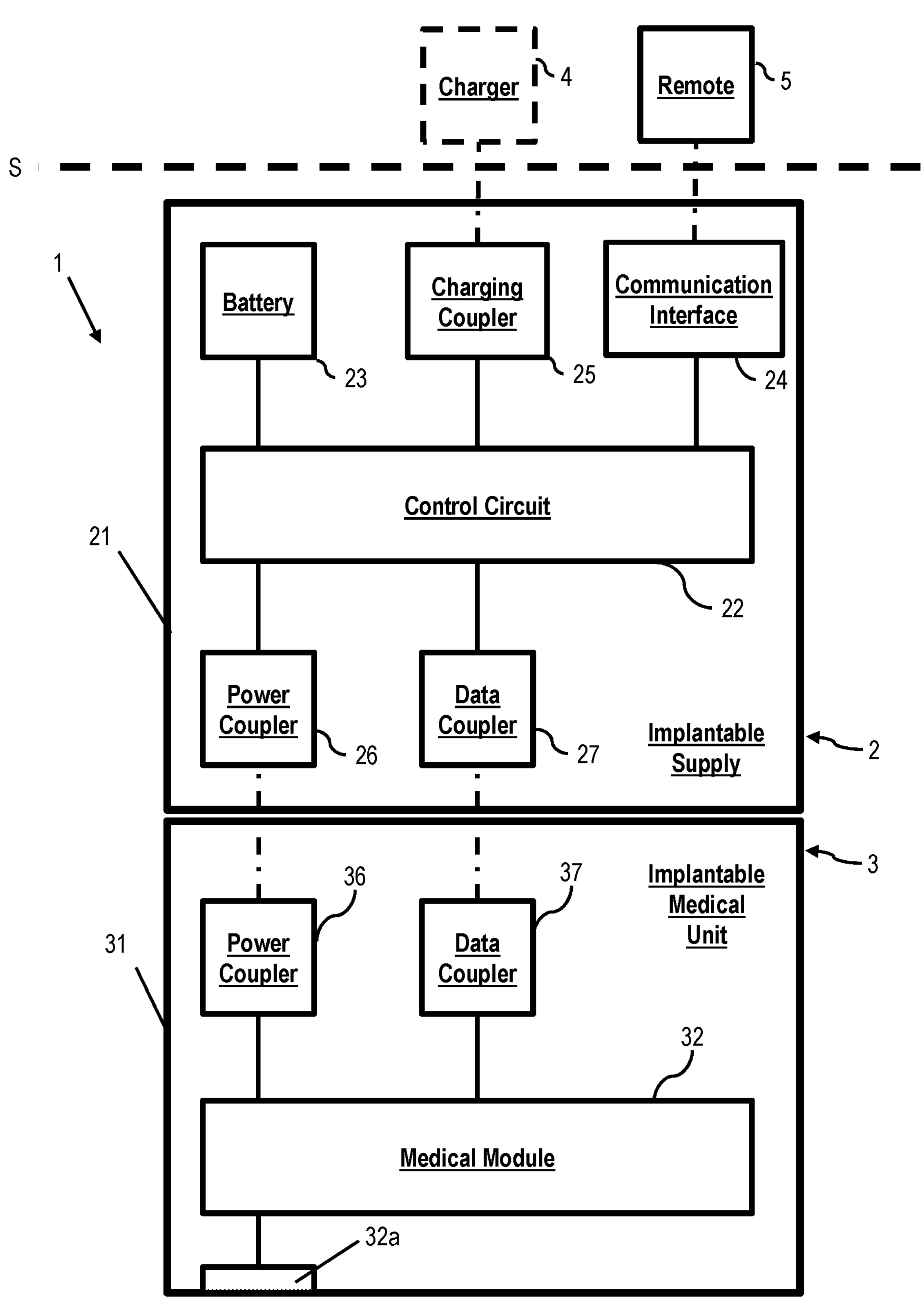
FIG. 1 shows an implantable medical device in a schematic functional view.

FIG. 1 shows an embodiment of an implantable medical device 1 in a schematic functional view and in an implanted state respectively in a situation of use. In FIG. 1, individual units or modules are shown as boxes. Operative couplings by way of galvanic coupling are shown as solid lines, while operative couplings by way of non-galvanic, particularly, wireless coupling, are shown as chain lines. It is noted that the shown functional units or modules are not necessarily structurally distinct from each other but may be realized in a fully or partly integral way.

The hermetically sealed implantable supply housing 21 encloses the control circuit 22, the battery 23, the implantable supply communication interface 24, the implantable supply power coupler 26 and the implantable supply data coupler 27. In embodiments where the battery 23 is rechargeable, the implantable supply 2 optionally further includes a charging coupler 25 for charging the battery 23 in the implanted state. As explained before in the general description, the implantable supply power coupler 26 and the implantable supply data coupler 27 may in some embodiments be realized integral with each other. Similarly, the implantable supply communication interface 24 and the optional charging coupler 25 may in some embodiments be formed integral with each other.

The hermetically sealed medical unit housing 31 encloses a functional medical module 32, a medical unit power coupler 36 and a medical unit data coupler 37. The functional medical module 32 is, by way of example, a continuous glucose meter module, but may additionally or alternatively also implement other medical functions as explained in the general description. The functional medical module 32 further includes sensing and/or stimulation electrodes that are separately shown as electrodes 32*a* in FIG. 1 for clarity reasons. The electrodes 32*a* contact the surrounding tissue in an implanted state. The sensing arrangements alternatively may be of optical nature e.g. by sending light into the tissue and receiving the scattered or induced fluorescing light.

As user interface for controlling operation of the implantable medical device 1 and/or displaying and further processing data that are acquired or measured by the implantable medical device 1, a remote device (also referred to as a "remote" or "remote control") 5 is provided. The remote device 5 is not part of the implantable medical device. The remote device 5 and the supply unit communication interface 24 may operatively couple and exchange data transcutaneously, with the skin being schematically shown as "S". It is noted that the remote device 5 does not need to be present continuously and/or continuously couple with the supply unit communication interface 24, but only in situations where data need to be exchanged. In particular in embodiments where the functional medical module is or includes a measuring module for a body parameter, such as a continuous glucose measurement module, the supply unit 2 and/or the medical unit 3 may be designed to store measured data, e.g., measured glucose data, and transmit them to the remote device 5 from time to time, e.g., upon user command.

In embodiments with a charging coupler 25 as explained before, an external charging device 4 may be provided that is designed to transmit power transcutaneous to the charging coupler 25, e.g., by way of inductive coupling. The charging device 4 is placed on the skin in close proximity to the supply unit 2 and in particular the charging coupler 25 from time to time for charging the battery 23, e.g., during night time.

Figure 2:
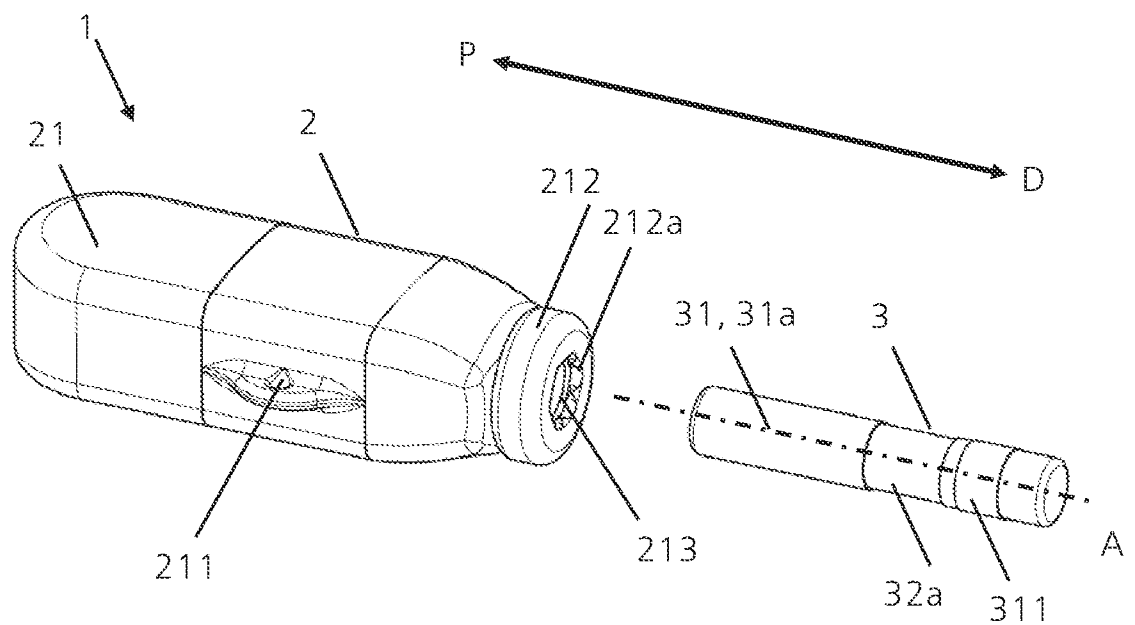
FIG. 2 shows an implantable medical device in a perspective view.

FIG. 2 shows an embodiment of an implantable medical device 1 in a perspective view. The implantable device may for example correspond to the embodiment of FIG. 1. In FIG. 2, the supply unit 2 and the medical unit 3 are shown in a relative orientation that corresponds to a situation of use. However, the medical unit 3 is shown as uncoupled with respect to the supply unit 2.

In this example, the supply unit 2 and the medical unit 3 both extend along a common longitudinal axis A. Opposing directions along the longitudinal axis A are referred to as proximal (towards the supply unit 2, indicated as "P"), respectively distal (towards the medical unit 3, indicated as "D").

The hermetically sealed supply unit housing 21 of the supply unit 2 comprises an exemplary substantially cylindrical receiving recess 213 that exemplarily extends along the longitudinal axis A. A distal end section of the receiving recess 213 is formed by a circumferential resilient sleeve 212. In this example, the hermetically sealed medical unit housing 31 is also substantially cylindrical. The medical unit housing 31 includes an elongated medical unit housing member 31*a* as proximal portion. At least a portion of the elongated medical unit housing member 31 is received by the receiving recess 213 in a coupled state. The outer diameter of the elongated medical unit housing member 31*a* corresponds to the inner diameter of the receiving recess 213 such that it is insertable into the receiving recces 213 with little or substantially no play by displaying the medical unit 3 in proximal direction along the longitudinal axis A. Due to its resilient properties, the sleeve 212 fixes the medical unit 3 by way of force locking. The receiving recess 213 and the sleeve 212 accordingly serve as supply unit coupling arrangement, while the corresponding elongated medical unit housing member 31*a* serves as medical unit coupling arrangement.

In this embodiment, the sleeve 212 does not need to hermetically seal the receiving recess 213 against the entry of body liquids. In typical application scenarios where the supply unit 2 has a longer lifetime as compared to the medical unit 3, body liquids may enter the receiving recess 213 when the medical unit is explanted for the purpose of replacement, while the supply unit 2 remains implanted. The sleeve 212 may be provided with openings that allow fluidic communication of the receiving recess 213 with the exterior, such body liquids are displaced out of the receiving recess 213 when a new medical unit 3 is connected. In the shown embodiment, openings are exemplary realized by longitudinal channels (not individually referenced) in the circumferential inner contact surface 212*a* that contacts the elongated medical unit housing member 31*a* in the coupled state.

Further in this example, the supply unit housing 21 comprises optional fixing elements that are realized by fixing eyes 211 on opposite sides of the supply unit housing 21. The fixing eyes 211 serve for fixing the supply unit 2 in the tissue by sewing it to solid tissue structures to prevent it from drifting around in the subcutaneous fat tissue. In this way, the supply unit provides a solid basis for the medical unit 3. Further, the fixing allows a simple location of the supply unit 2 at the end of its lifetime since it cannot move within the body during its application time.

Further in this example, the medical unit housing 31 comprises an optional ring-shaped circumferential anti-inflammatory element 311 that is made from silicone rubber with an embedded anti-inflammatory agent. The anti-inflammatory element 311 is arranged in a distal section of the medical unit housing that is not inserted into the receiving recess 213. Alternatively or additionally, the sleeve 212 may comprise an embedded anti-inflammatory agent, thereby serving as anti-inflammatory element. Anti-inflammatory elements prevent an undesired encapsulation by body tissue over an extended time period.

The electrodes 32*a* are arranged on the circumference of the medical unit housing 31 in the area that is not inserted into the receiving recess 213.

Figure 3:
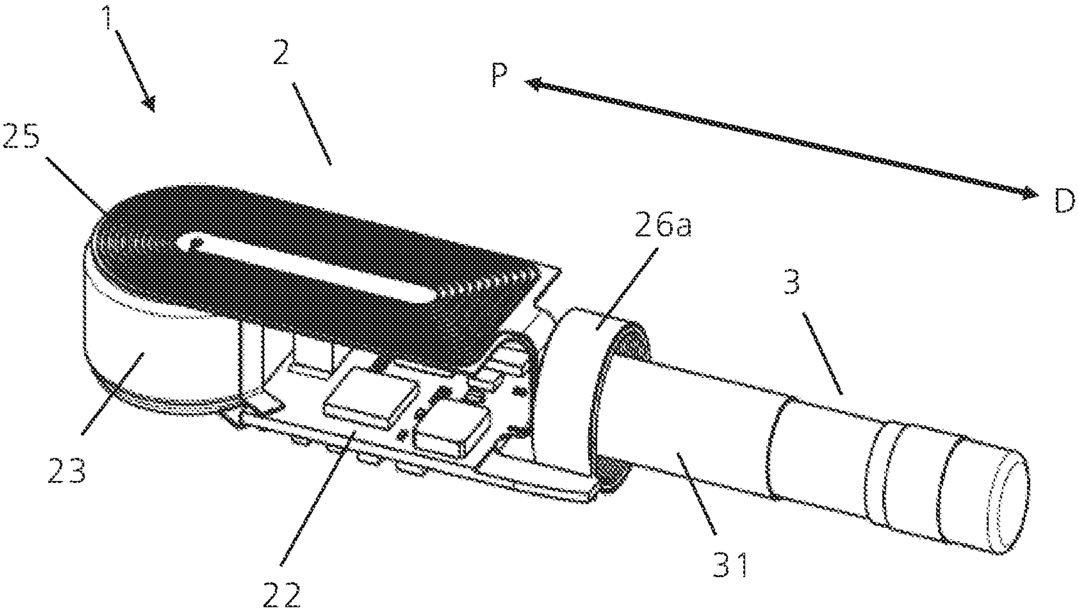
FIG. 3 shows a further perspective view of the medical device of FIG. 2.

FIG. 3 shows the implantable medical device 1 of FIG. 2 in a further view. In FIG. 3, the medical unit 3 and the supply unit 2 are shown in the mechanically coupled state where a proximal portion of the medical unit housing 31 is located inside the receiving recess 313 as explained before. Further in FIG. 3, the supply unit housing 21 is removed.

The battery 23 which is in this example rechargeable is exemplarily arranged in a proximal section of the supply unit 2. For transcutaneous battery charging, a charging coupler is 25 is provided in form of a flat coil. The coil 25 is favorably arranged on a side of the supply unit 2 that faces, in an implanted state, towards the skin and substantially parallel to the skin, thereby enabling good inductive coupling with an external charging device 4 as explained before.

Further, a medical unit NFC coil 26*a* is circumferentially arranged around a portion of the receiving recess 213. The medical unit NFC coil 26*a* serves as both supply unit power coupler coil of the supply unit power coupler 26 and supply unit data coupler coil of the supply unit data coupler 27 in an integral way.

A printed circuit board with electronics component serves as control circuit 22 and carries, among others, the supply unit communication interface 24 as well as further circuitry for charging the battery 23, providing power to and communicating with the medical unit 3.

Figure 4:
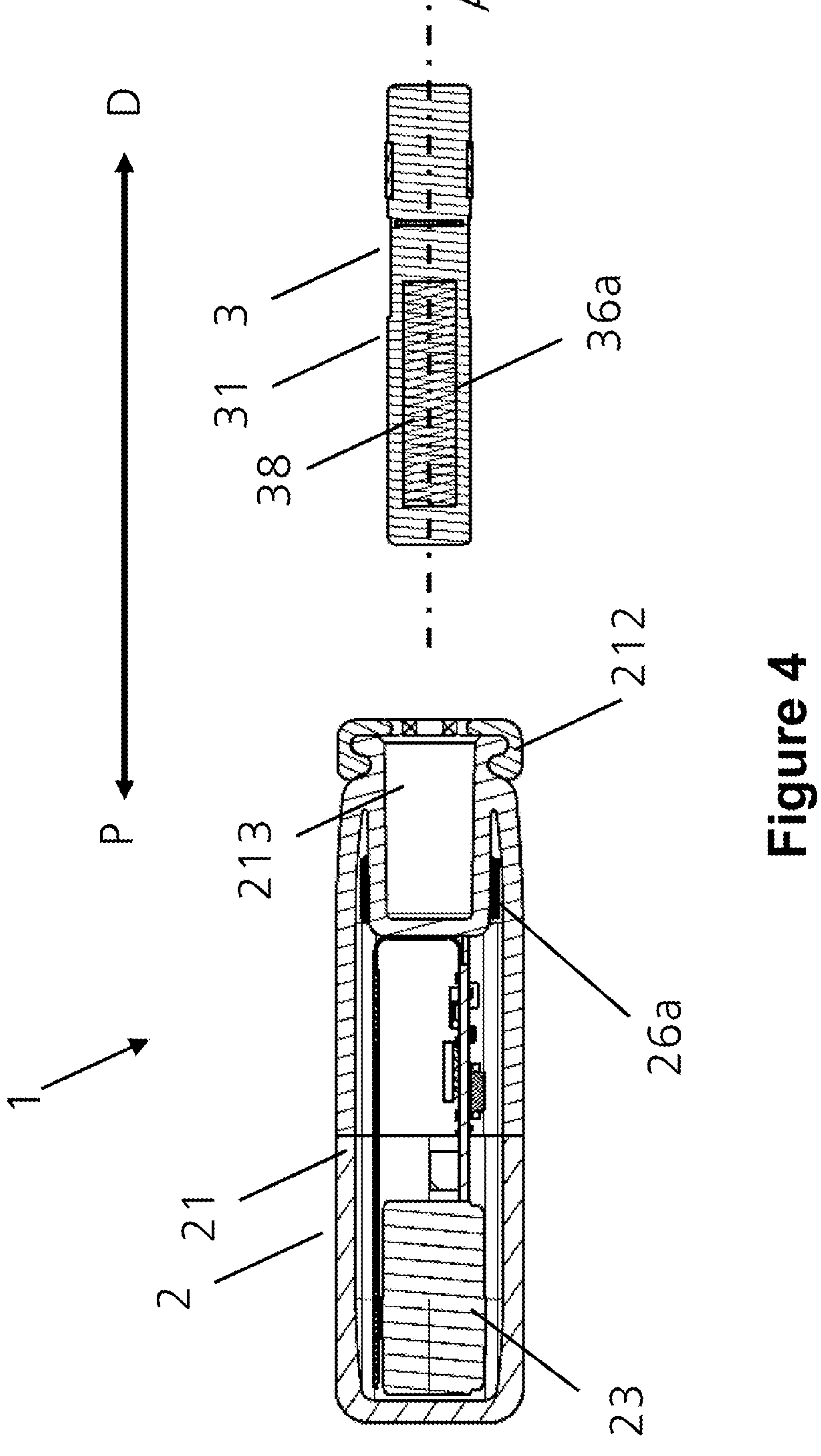
FIG. 4 shows a sectional view of the medical device of FIG. 1.
Figure 5:
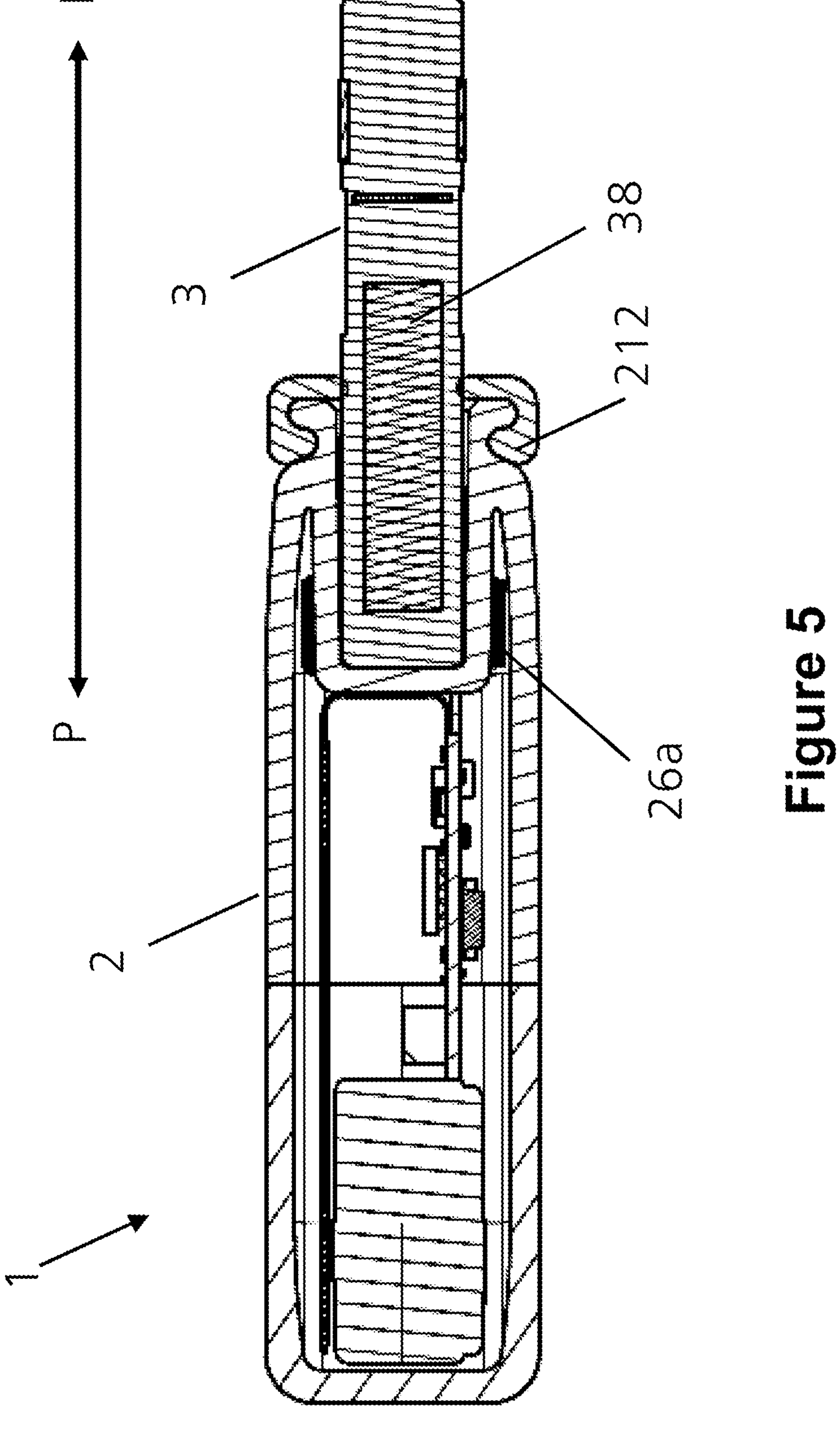
FIG. 5 shows a further sectional view of the medical device of FIG. 1.

FIG. 4 shows the implantable medical device 1 in a sectional view and a corresponding configuration where the supply unit 2 and the medical unit 3 are uncoupled (like in FIG. 2). FIG. 5 is similar to FIG. 4 and shows the medical device 1 in a configuration where the supply unit 2 and the medical unit 3 are coupled to each other, corresponding to a situation of use. The medical unit 3 comprises a rod-shaped ferrite core 38 that is arranged along the longitudinal axis A inside the medical unit housing 31. The ferrite core 38 is positioned such that at least part of its length is located inside the receiving recess 213 in a coupled state of the supply unit 2 and the medical unit 3. The medical unit power coupler 36 and the medical unit data coupler 37 are in this embodiment realized by a common NFC arrangement with a medical unit NFC coil 36*a* that is circumferentially arranged around the ferrite core 38 and serves as both medical unit power coupler coil and medical unit data coupler coil. The ferrite core 38 and the NFC coil 36*a* may form, in combination, a compact NFC module. In the coupled state of the supply unit 2 and the medical unit 3, the ferrite core 38 ensures good inductive coupling between the supply unit NFC coil 26*a* and the medical unit NFC coil 36*a*, respectively, thereby ensuring safe and efficient power transmission from the supply unit 2 to the medical unit 3 as well as data communication between the units.

While exemplary embodiments have been disclosed hereinabove, the present invention is not limited to the disclosed embodiments. Instead, this application is intended to cover any variations, uses, or adaptations of this disclosure using its general principles. Further, this application is intended to cover such departures from the present disclosure as come within known or customary practice in the art to which this invention pertains and which fall within the limits of the appended claims.

LIST OF DESIGNATIONS

1 implantable medical device
2 implantable supply unit
21 supply unit housing
22 control circuit
23 battery
24 supply unit communication interface
25 charging coupler
26 supply unit power coupler
26*a* supply unit NFC coil
27 supply unit data coupler
211 fixing eye
212 sleeve
212*a* circumferential inner contact surface
213 receiving recess
3 implantable medical unit
31 medical unit housing
31*a* elongated medical unit housing member
32 functional medical module/continuous glucose meter module
32*a* electrodes
36 medical unit power coupler
36*a* medical unit NFC coil
37 medical unit data coupler
38 ferrite core
311 anti-inflammatory element
4 charging device
5 remote device
A longitudinal axis
S skin
D distal direction
P proximal direction

What is claimed is:

1. An implantable medical device, comprising:

an implantable supply and an implantable sensor, the implantable supply further comprising:

a hermetically sealed supply housing;

a battery;

a wireless supply power coupler configured for powering the implantable sensor from the battery via wireless coupling;

a wireless supply data coupler configured for wireless data communication with the sensor;

a wireless supply communication interface configured for wireless communication with a non-implanted remote control; and a supply coupling arrangement configured for releasably mechanically coupling the sensor to the implantable supply;

wherein the battery, the supply power coupler, the supply data coupler and the supply communication interface are enclosed by the supply housing;

the implantable sensor comprising:

a hermetically sealed sensor housing;

a continuous glucose meter;

a wireless sensor power coupler configured to receive power from the supply power coupler by wireless coupling, thereby powering the sensor;

a wireless sensor data coupler configured for wireless data communication with the supply; and a sensor coupling arrangement that mates with the supply coupling arrangement;

wherein the supply coupling arrangement includes a receiving recess in the supply housing configured for receiving at least part of the sensor, the sensor coupling arrangement including a proximal end received within the supply coupling arrangement in radial spaced relation to the supply coupling arrangement to define a non-galvanic coupling;

wherein the battery is rechargeable and the implantable supply includes a wireless charging coupler configured for wireless charging of the battery from the non-implanted remote control in an implanted state of the implantable supply;

wherein the receiving recess of the supply coupling arrangement in the supply housing is configured for receiving the proximal end of the sensor coupling arrangement;

wherein at least part of the sensor housing is inserted into the supply housing, and at least part of the continuous glucose meter extends outside of the supply housing distal of the sensor coupling arrangement.

2. The implantable medical device according to claim 1, wherein the wireless supply power coupler includes a supply power coupler coil and the wireless sensor power coupler includes a corresponding sensor power coupler coil.

3. The implantable medical device according to claim 2, wherein the implantable sensor includes a ferromagnetic coupling member and the sensor power coupler coil is arranged circumferentially around the ferromagnetic coupling member.

4. The implantable medical device according to claim 3, wherein the sensor housing includes an elongated member enclosing the ferromagnetic coupling member and wherein the supply housing includes the receiving recess configured to receive at least part of the elongated member, and wherein the supply power coupler coil is arranged circumferentially around the receiving recess.

5. The implantable medical device according to claim 1, wherein the wireless supply power coupler and the wireless supply data coupler are integrally formed.

6. The implantable medical device according to claim 1, wherein the wireless charging coupler is formed integrally with the wireless supply communication interface.

7. The implantable medical device according to claim 1, wherein the wireless supply power coupler includes a supply power coupler coil.

8. The implantable medical device according to claim 7, wherein the supply power coupler coil is arranged circumferentially around the receiving recess.

9. A method for powering an implantable sensor, comprising:

providing an implantable medical device according to claim 1;

releasably mechanically coupling the implantable sensor and the implantable supply;

making a wireless coupling of the wireless sensor power coupler with the wireless supply power coupler, thereby powering the sensor from the battery of the implantable supply.

10. The method according to claim 9, wherein the wireless coupling is an inductive coupling.

11. The implantable medical device of claim 1, wherein the sensor housing is coaxially arranged with the supply housing.

12. An implantable medical device, comprising:

an implantable supply and an implantable sensor, the implantable supply further comprising:

a hermetically sealed supply housing;

a battery;

a supply power coupler configured for powering the implantable sensor from the battery via wireless coupling;

a supply data coupler configured for wireless data communication with the sensor;

a supply communication interface configured for wireless communication with a non-implanted remote control; and a supply coupling arrangement configured for releasably mechanically coupling the sensor to the implantable supply;

wherein the battery, the supply power coupler, the supply data coupler and the supply communication interface are enclosed by the supply housing;

the implantable sensor comprising:

a hermetically sealed sensor housing;

a continuous glucose meter;

a sensor power coupler configured to receive power from the supply power coupler by wireless coupling, thereby powering the sensor;

wherein the supply power coupler receives a proximal end of the glucose meter to wirelessly couple with the sensor power coupler;

a sensor data coupler configured for wireless data communication with the supply; and a sensor coupling arrangement that mates with the supply coupling arrangement, the sensor coupling arrangement including a proximal end received within the supply coupling arrangement in radial spaced relation to the supply coupling arrangement to define a non-galvanic coupling;

wherein the supply coupling arrangement includes a receiving recess in the supply housing configured for receiving the proximal end of the sensor coupling arrangement, wherein at least part of the sensor housing is inserted into the supply housing, and at least part of the continuous glucose meter extends outside of the supply housing distal of the sensor coupling arrangement.

13. The implantable medical device of claim 12, wherein the battery is rechargeable and the implantable supply includes a charging coupler configured for wireless charging of the battery in an implanted state of the implantable supply.

14. The implantable medical device of claim 12, wherein the sensor housing is coaxially arranged with the supply housing.

15. The implantable medical device according to claim 12, wherein the supply power coupler includes a supply power coupler coil and the sensor power coupler includes a corresponding sensor power coupler coil.

16. The implantable medical device according to claim 15, wherein the implantable sensor includes a ferromagnetic coupling member and the sensor power coupler coil is arranged circumferentially around the ferromagnetic coupling member.

17. The implantable medical device according to claim 16, wherein the sensor housing includes an elongated member enclosing the ferromagnetic coupling member and wherein the supply housing includes the receiving recess configured to receive at least part of the elongated member, and wherein the supply power coupler coil is arranged circumferentially around the receiving recess.

18. The implantable medical device according to claim 12, wherein the wireless supply power coupler includes a supply power coupler coil.

19. The implantable medical device according to claim 12, wherein the supply coupling arrangement includes the receiving recess in the supply housing for receiving at least part of the sensor.

20. The implantable medical device according to claim 19, wherein the supply power coupler coil is arranged circumferentially around the receiving recess.

* * * * *